United States Patent [19]

Moore et al.

[11] Patent Number: 5,362,477

[45] Date of Patent: *Nov. 8, 1994

[54] 19F MAGNETIC RESONANCE IMAGING AGENTS WHICH INCLUDE A NITROXIDE MOIETY

[75] Inventors: Dennis A. Moore, Ferguson; Max D. Adams, St. Charles; William P. Cacheris, Florissant; David H. White, Ballwin; Muthunadar P. Periasamy, Chesterfield; Raghavan Rajagopalan, Maryland Heights; Lynn A. deLearie, University City; Steven R. Woulfe, Ballwin, all of Mo.

[73] Assignee: Mallinckrodt Medical, Inc., St. Louis, Mo.

[*] Notice: The portion of the term of this patent subsequent to Nov. 23, 2010 has been disclaimed.

[21] Appl. No.: 950,343

[22] Filed: Dec. 1, 1992

Related U.S. Application Data

[63] Continuation-in-part of Ser. No. 826,333, Jan. 27, 1992, abandoned, which is a continuation-in-part of Ser. No. 782,153, Oct. 25, 1991, Pat. No. 5,318,770.

[51] Int. Cl.$^5$ ............................................. A61B 5/055
[52] U.S. Cl. ........................................ 424/9; 436/173; 128/653.4; 514/329; 514/331; 514/422; 514/832; 546/224; 546/225; 546/233; 548/537; 548/542

[58] Field of Search ............................. 424/9; 436/173; 128/653.4, 654; 514/329, 331, 422, 832; 546/224, 225, 233; 548/537, 542

[56] References Cited

U.S. PATENT DOCUMENTS

| | | | |
|---|---|---|---|
| 4,612,185 | 9/1986 | Dean | 424/2 |
| 4,639,364 | 1/1987 | Hoey | 424/9 |
| 5,104,641 | 4/1992 | Rosen | 424/9 |
| 5,116,599 | 5/1992 | Rogers, Jr. et al. | 424/9 |

OTHER PUBLICATIONS

Church, D. F. *J. Organic Chemistry* 51(7):1138–40 (1986).
Boymel, P. M. *Inorganic Chemistry* 19(3):735–9 (1980).
Eaton, S. S. *J. Magnetic Resonance* 56:183–199 (1984).

*Primary Examiner*—Gary E. Hollinden
*Attorney, Agent, or Firm*—Brian K. Stierwalt

[57] ABSTRACT

Methods and compositions are disclosed for enhancing $^{19}F$ magnetic resonance imaging which utilize $^{19}F$ magnetic resonance contrast media having enhanced $^{19}F$ relaxivity. Fluorine-containing compounds having enhanced $^{19}F$ relaxation properties resulting from direct association with an unpaired spin are disclosed. The fluorine-containing compound is associated with the unpaired spin by covalent attachment of a stable free radical, by complexation of a fluorinated complexing agent with a paramagnetic metal ion, or by salt formation or charge neutralization of a paramagnetic ion.

8 Claims, No Drawings

19F MAGNETIC RESONANCE IMAGING AGENTS WHICH INCLUDE A NITROXIDE MOIETY

CROSS REFERENCE TO RELATED APPLICATION

This invention is a continuation-in-part of U.S. patent application Ser. No. 07/826,333, filed Jan. 27, 1992, abandoned, titled "$^{19}$F Magnetic Resonance Imaging Agents With Enhanced $^{19}$F Relaxivity," which is a continuation-in-art of U.S. patent application Ser. No. 07/782,153 now U.S. Pat. No. 5,318,770, filed Oct. 25, 1991, titled "Trifluoromethyl Analogs of X-ray Contrast Media for Magnetic Resonance Imaging."

BACKGROUND OF THE INVENTION

This invention relates to compositions for improving fluorine-19 magnetic resonance imaging ("MRI"), including magnetic resonance spectroscopy ("MRS") and magnetic resonance spectroscopy imaging ("MRSI") techniques. More particularly, the present invention relates to fluorine-19 imaging agents having paramagnetic species directly associated with the imaging agent for improving fluorine-19 relaxation times.

The technique of MRI encompasses the detection of certain atomic nuclei (those possessing magnetic dipole moments) utilizing magnetic fields and radio-frequency radiation. It is similar in some respects to x-ray computed tomography ("CT") in providing a cross-sectional display of the body organ anatomy with excellent resolution of soft tissue detail. The technique of MRI is advantageously non-invasive as it avoids the use of ionizing radiation.

The hydrogen atom, having a nucleus consisting of a single unpaired proton, has the strongest magnetic dipole moment of any nucleus. Since hydrogen occurs in both water and lipids, it is abundant in the human body. Therefore, MRI is most commonly used to produce images based upon the distribution density of protons and/or the relaxation times of protons in organs and tissues. Other nuclei having a net magnetic dipole moment also exhibit a nuclear magnetic resonance phenomenon which may be used in MRI, MRS, and MRSI applications. Such nuclei include carbon-13 (six protons and seven neutrons), fluorine-19 (9 protons and 10 neutrons), sodium-23 (11 protons and 12 neutrons), and phosphorus-31 (15 protons and 16 neutrons).

While the phenomenon of NMR was discovered in 1945, it is only relatively recently that it has found application as a means of mapping the internal structure of the body as a result of the original suggestion of Lauterbur (*Nature*, 242, 190–191 (1973)). The fundamental lack of any known hazard associated with the level of the magnetic and radio-frequency fields that are employed renders it possible to make repeated scans on vulnerable individuals. Additionally, any scan plane can readily be selected, including transverse, coronal, and sagittal sections.

In an MRI experiment, the nuclei under study in a sample (e.g. protons, $^{19}$F, etc.) are irradiated with the appropriate radio-frequency (RF) energy in a controlled gradient magnetic field. These nuclei, as they relax, subsequently emit RF energy at a sharp resonance frequency. The resonance frequency of the nuclei depends on the applied magnetic field.

According to known principles, nuclei with appropriate spin when placed in an applied magnetic field (B, expressed generally in units of gauss or Tesla ($10^4$ gauss)) align in the direction of the field. In the case of protons, these nuclei precess at a frequency, F, of 42.6 MHz at a field strength of 1 Tesla. At this frequency, an RF pulse of radiation will excite the nuclei and can be considered to tip the net magnetization out of the field direction, the extend of this rotation being determined by the pulse, duration and energy. After the RF pulse, the nuclei "relax" or return to equilibrium with the magnetic field, emitting radiation at the resonant frequency. The decay of the emitted radiation is characterized by two relaxation times, $T_1$ and $T_2$. $T_1$ is the spin-lattice relaxation time or longitudinal relaxation time, that is, the time taken by the nuclei to return to equilibrium along the direction of the externally applied magnetic field. $T_2$ is the spin-spin relaxation time associated with the dephasing of the initially coherent precession of individual proton spins. These relaxation times have been established for various fluids, organs, and tissues in different species mammals.

For protons and other suitable nuclei, the relaxation times $T_1$ and $T_2$ are influenced by the environment of the nuclei (e.g., viscosity, temperature, and the like). These two relaxation phenomena are essentially mechanisms whereby the initially imparted radio-frequency energy is dissipated to the surrounding environment. The rate of this energy loss or relaxation can be influenced by certain molecules or other nuclei which are paramagnetic. Chemical compounds incorporating these paramagnetic molecules or nuclei may substantially alter the $T_1$ and $T_2$ values for nearby nuclei having a magnetic dipole moment. The extent of the paramagnetic effect of the given chemical compound is a function of the environment within which it finds itself.

In general, paramagnetic ions of elements with an atomic number of 21 to 29, 42 to 44 and 58 to 70 have been found effective as MRI contrasting agents. Suitable such ions include chromium(III), manganese(II), iron(III), iron (II), cobalt (II), nickel (II), copper (II), praseodymium(III), neodymium(III), samarium(III) and ytterbium(III). Because of their very strong magnetic moments, gadolinium(III), terbium(III), dysprosium(III), holmium(III) and erbium(III) are preferred. Gadolinium(III) ions have been particularly preferred as MRI contrasting agents.

In MRI, scanning planes and sliced thicknesses can be selected. This selection permits high quality transverse, coronal and sagittal images to be obtained directly. The absence of any moving parts in MRI equipment promotes a high reliability. It is believed that MRI has a greater potential than CT for the selective examination of tissue characteristics. The reason for this being that in CT, X-ray attenuation and coefficients alone determine image contrast, whereas at least four separate variables ($T_1$, $T_2$, proton density, and flow) may contribute to the MRI signal. For example, it has been shown (Damadian, *Science*, 171, 1151 (1971)) that the values of the $T_1$ and $T_2$ relaxation in tissues are generally longer by about a factor of two (2) in excised specimens of neoplastic tissue compared with the host tissue.

By reason of its sensitivity to subtle physiochemical differences between organs and/or tissues, it is believed that MRI may be capable of differentiating different tissue types and in detecting diseases which induce physicochemical changes that may not be detected by X-ray or CT which are only sensitive to differences in the electron density of tissue.

In some cases, the concentration of nuclei to be measured is not sufficiently high to produce a detectable MR signal. For instance, since $^{19}$F is present in the body in very low concentration, a fluorine source must be administered to a subject to obtain a measurable $^{19}$F MR signal. Signal sensitivity is improved by administering higher concentrations of fluorine or by coupling the fluorine to a suitable "probe" which will concentrate in the body tissues of interest. High fluorine concentration must be balanced against increased tissue toxicity. It is also currently believed that a fluorine agent should preferably contain magnetically equivalent fluorine atoms in order to obtain a clear, strong signal.

From the foregoing, it would be a significant advancement in the art to provide fluorine MRI agents for enhancing images of body organs and tissues which may be administered in relatively low concentrations, yet provide a clear, strong signal.

Such MRI agents are disclosed and claimed herein.

SUMMARY OF THE INVENTION

The present invention provides methods and compositions for improved fluorine-19 magnetic resonance imaging and spectroscopy in which paramagnetic species are directly associated with the fluorine-19 imaging agent for improving fluorine-19 relaxation times. The paramagnetic species include paramagnetic metal ions and stable free radicals.

The compounds of the present invention include fluorine-containing compounds having enhanced relaxation properties resulting from direct association with an unpaired spin. The unpaired spin may be directly associated with the fluorine compound by covalent attachment of a stable free radical, by complexation of a paramagnetic metal ion, or by salt formation or charge neutralization of a paramagnetic ion.

One class of MRI agents within the scope of the present invention are spin labelled CF$_3$ derivatives of known iodinated X-ray contrast media ("XRCM"). Various CF$_3$-containing magnetic resonance contrast media ("MRCM") which may be spin labelled according to the present invention are described in greater detail in copending application Ser. No. 07/782,153, which is incorporated by reference.

Typical CF$_3$ analogs of XRCM within the scope of the present invention include spin labelled bis(trifluoromethyl)benzene derivatives, tris(trifluoromethyl)benzene derivatives, tetrakis(trifluoromethyl)benzene derivatives, and other related trifluoromethylated benzene derivatives having a stable free radical bound thereto.

An example of a spin labelled CF$_3$ derivative of XRCM is shown below:

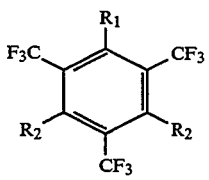

Where R$_1$ is CONR$_3$R$_4$, NR$_3$R$_4$, or NHCOCH$_2$NR$_3$R$_4$; R$_2$ is CONHR$_3$, NHCOCH$_2$NHR$_3$, NHR$_3$, CO$_2$$^-$, or CO$_2$H; R$_3$ is H or a hydroxyalkyl group having from 1 to 6 carbon atoms; and R$_4$ is any stable free radical, such as a nitroxide free radical. As used herein, the term nitroxide free radical includes physiologically stable compounds having the general structure R$_5$R$_6$N—O.; wherein R$_5$ and R$_6$ may be alkyl, hydroxyalkyl, alkoxyalkyl, and wherein R$_5$ and R$_6$ may optionally be joined together to form a 5 to 7 member heterocyclic ring with the nitroxide nitrogen atom. Examples of some possible stable nitroxide radicals which may be used within the scope of the present invention are described in U.S. Pat. No. 4,925,652 to Gries et al. and in EP 0 375 074 to Hafslund Nycomed Innovation AB, which are hereby incorporated by reference.

The present invention further includes fluorine-containing compounds having a stable free radical substituent. The following fluorine-containing compound is one example of such compounds within the scope of the present invention:

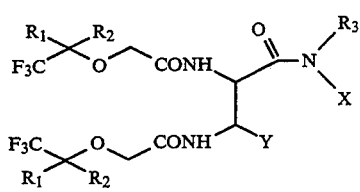

Where R$_1$ and R$_2$ may be the same or different and are CF$_3$ or simple alkyl groups. R$_3$ is selected from the group consisting of H, alkyl and hydroxyalkyl. X is any stable free radical, such as a nitroxide free radical described above. Y is —CONR$_4$R$_5$, —CO$_2$H, or pharmaceutically acceptable salts thereof, and where R$_4$ and R$_5$ are from the group consisting of H, alkyl and hydroxyalkyl, with preferably at least one being hydroxyalkyl.

The present invention also includes fluorine-containing free radicals and compounds substituted with fluorine-containing free radicals. Stable free radicals, such as nitroxide, phenoxy, and phenoxazinyl free radicals are substituted with CF$_3$, or similar fluorine group, to form fluorine-containing free radicals within the scope of the present invention. Since stable free radicals are paramagnetic, it is believed that the free radical will enhance the relaxation properties of nearby fluorine nuclei.

One possible fluorine-containing nitroxide radical within the scope of the present invention is shown below:

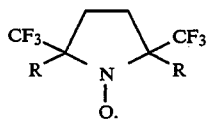

Where R is CF$_3$, alkyl, hydroxyalkyl, alkoxyalkyl or perfluoro-t-butyl (—C(CF$_3$)$_3$).

Fluorine-containing free radicals of the present invention may replace the iodine of known triiodinated benzene XRCM to prepare a new class $^{19}$F MRCM. As an example, a trisubstituted benzene derivative having fluorinated nitroxide radicals described above would have from 18 to 36 $^{19}$F nuclei for magnetic resonance imaging.

The MRCM of the present invention also include fluorinated paramagnetic complexes. Such complexes may be prepared by complexing paramagnetic metal ions with fluorine-containing complexing agents. Typical complexing agents which may be used within the scope of the present invention include the class of fluorine-containing linear or cyclic polyamino-polycarboxylic acids and their derivatives including ester, amide, and amine derivatives. Other complexing agents containing fluorine groups, such as phosphonates, phenolates, and carboxylates are also within the scope of the present invention.

Another class of fluorine-19 MRCM within the scope of the present invention are paramagnetic ion salts of fluorinated compounds. Either the anion or cation can be the fluorinated compound. The paramagnetic ion may include paramagnetic metal ions and paramagnetic free radical ions.

Also disclosed are diagnostic compositions and methods of performing MR diagnostic procedures which involve administering to a warm-blooded animal a diagnostically effective amount of the above-described fluorine substituted MRCM compositions and then exposing the warm-blooded animal to a MR procedure.

DETAILED DESCRIPTION OF THE INVENTION

The present invention provides novel fluorine-19 MRCM having paramagnetic species directly associated with the imaging agent to improve fluorine-19 relaxation times. The MRCM of the present invention include spin labelled trifluoromethyl derivatives of XRCM and other spin labelled fluorine-containing compounds. The present invention also includes derivatives of triiodinated benzene XRCM in which iodine is replaced by a fluorine containing nitroxide radical. The MRCM of the present invention also include fluorinated paramagnetic complexes and salts of paramagnetic metal ions and fluorinated compounds.

For example, spin labelling various $CF_3$ derivatives of triiodobenzene XRCM result in $^{19}F$ MRCM in which the $^{19}F$ relaxation time, $T_1$, is significantly decreased. Typical spin labelled trifluoromethyl XRCM derivatives within the scope of the present invention include (a) bis(trifluoromethyl)benzene derivatives, (b) tris(trifluoromethyl)benzene derivatives, (c) tetrakis(trifluoromethyl)benzene derivatives, and (d) other related trifluoromethylated benzene derivatives. Generic structures for these spin labelled trifluoromethyl MRCM compounds follows:

(a) Spin labelled bis(trifluoromethyl)benzene derivatives:

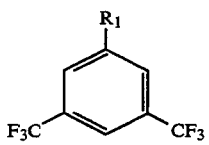

where $R_1$ may be $-CONR_3R_4$, $-NR_3R_4$, $-NHCOCH_2NR_3R_4$, and pharmaceutically acceptable salts thereof; $R_3$ may be H or hydroxyalkyl; and $R_4$ is a stable free radical, such as a nitroxide free radical. The following is an example of a spin labelled bis(trifluoromethyl)benzene derivative within the scope of the present invention:

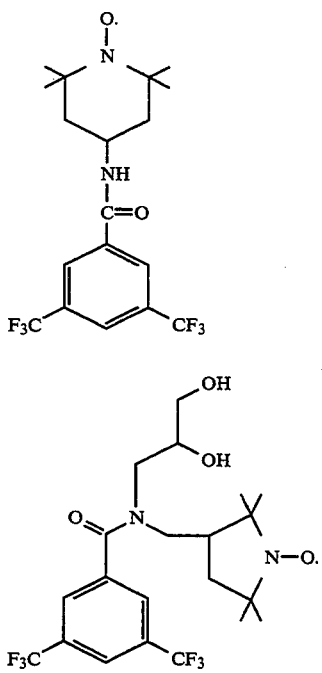

(b) Spin labelled tris(trifluoromethyl)benzene derivatives:

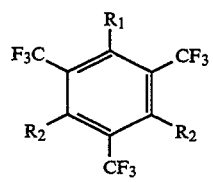

Where $R_1$ is $CONR_3R_4$, $NR_3R_4$, or $NHCOCH_2NR_3R_4$; $R_2$ is $CONHR_3$, $NHCOCH_2NHR_3$, $NHR_3$, $CO_2^-$, or $CO_2H$; $R_3$ is H or a hydroxyalkyl group; and $R_4$ is a stable free radical, such as a nitroxide free radical. The following is one possible example of a spin labelled tris(trifluoromethyl)benzene derivative within the scope of the present invention:

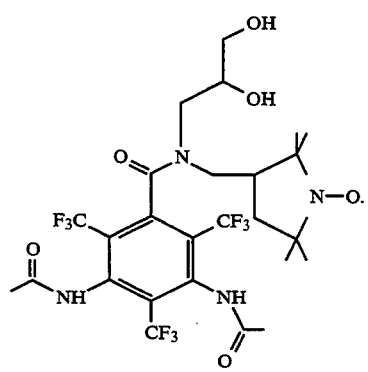

(c) Spin labelled tetrakis(trifluoromethyl)benzene derivatives:

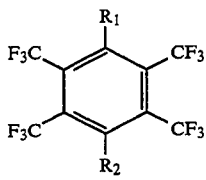

Where $R_1$ is $CONR_3R_4$, $NR_3R_4$, or $NHCOCH_2NR_3R_4$; $R_2$ is $CONHR_3$, $NHCOCH_2NHR_3$, $NHR_3$, $CO_2^-$, or $CO_2H$; $R_3$ is H or a hydroxyalkyl group; and $R_4$ is a stable free radical, such as a nitroxide free radical. The following is an example of a tetrakis(trifluoromethyl)-benzene derivative within the scope of the present invention:

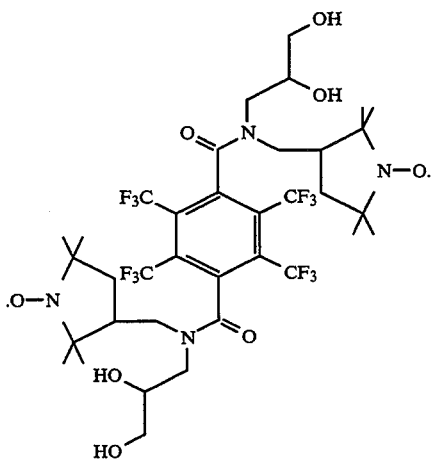

The spin labelled fluorine MRCM within the scope of the present invention are preferably prepared such that all the fluorines are substantially chemically equivalent to avoid imaging problems associated with non-equivalent nuclei. In addition, the spin labelled fluorine MRCM may be prepared with a large number of fluorine atoms per molecule, thereby improving the efficacy of the molecule and lowering the imaging dose. The present invention also includes fluorinated compounds which have been spin labelled with a stable free radical. The following generic compound illustrates possible spin labelled, fluorinated compounds within the scope of the present invention:

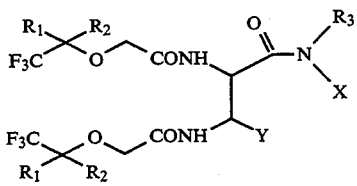

Where $R_1$ and $R_2$ may be the same or different and are $CF_3$ or simple alkyl groups. $R_3$ is selected from the group consisting of H, alkyl and hydroxyalkyl. X is any stable free radical, such as a nitroxide free radical described above. Y is $-CONR_4R_5$, $-CO_2H$, or pharmaceutically acceptable salts thereof, and where $R_4$ and $R_5$ are from the group consisting of H, alkyl and hydroxyalkyl, with preferably at least one being hydroxyalkyl.

One currently preferred spin labelled, fluorine-containing compound within the present invention follows:

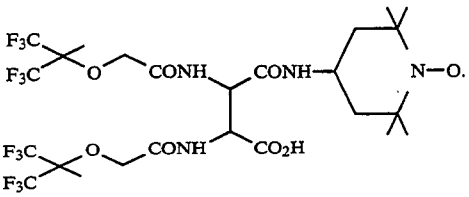

In another embodiment of the present invention, MRCM are prepared with fluorinated, stable free radicals, such as nitroxide, phenoxy, and phenoxazinyl free radicals. One possible $CF_3$ substituted nitroxide radical shown below:

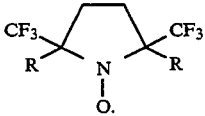

Where R is $CF_3$, alkyl, hydroxyalkyl, alkoxyalkyl or perfluoro-t-butyl ($-C(CF_3)_3$).

It is believed that the paramagnetic nitroxide radical will enhance the relaxation properties of nearby fluorine nuclei. A trisubstituted benzene moiety, as shown below, would have from 18 to 36 equivalent $^{19}F$ nuclei for imaging.

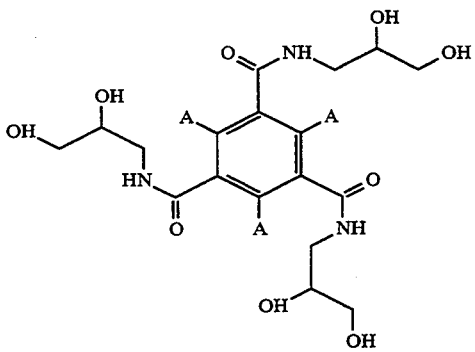

Where A has the following general formula:

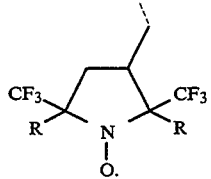

Where R is $CF_3$, alkyl, hydroxyalkyl, alkoxyalkyl or perfluoro-t-butyl ($-C(CF_3)_3$).

It will be appreciated by those skilled in the art that suitable fluorinated nitroxide radicals may replace the $CF_3$ groups in the bis, tris, and tetrakistrifluoromethyl-substituted benzene compounds and other spin labelled fluorine compounds identified above.

Stable phenoxy and phenoxazinyl radicals can be prepared from hindered phenols. The following are additional examples of fluorine-containing stable free radicals within the scope of the present invention:

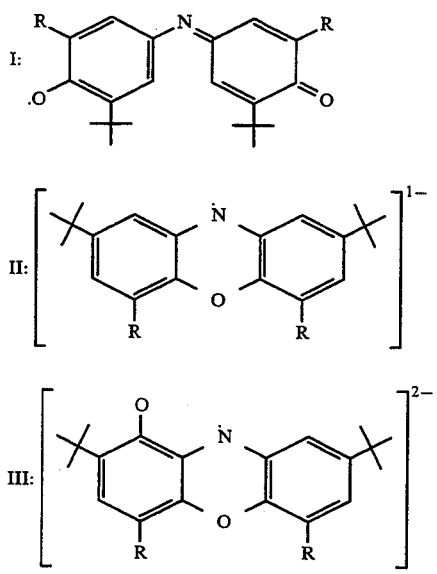

Where R may be CF₃ or perfluoro-t-butyl (—C(CF₃)₃). The synthetic reactions for the preparation of radicals I-III use substituted aminophenols as starting materials. It is believed the t-butyl substituents afford extra stability to the free radicals. Although not shown, the t-butyl substituents can be modified to increase the water solubility of these compounds. In addition, conventional water solubilizing groups, such as —SO₃,—OH, and hydroxyalkyl, may be added to radicals I-III to increase the water solubility.

The MRCM of the present invention also include fluorinated paramagnetic complexes. Such complexes may be prepared by combining paramagnetic metal ions with fluorine-containing complexing agents. In general, paramagnetic ions of elements with an atomic number of 21 to 29, 42 to 44 and 58 to 70 have been found effective as MRI contrasting agents. Suitable such ions include chromium (III), manganese (II), manganese (III), iron (III), iron(II), cobalt(II), nickel(II), copper(II), praseodymium(III), neodymium(III), samarium(III) and ytterbium(III) . Because of their very strong magnetic moments, gadolinium(III), terbium(III), dysprosium(III), holmium(III) and erbium(III) are preferred. Typical complexing agents which may be used within the scope of the present invention include the class of fluorine-containing linear or cyclic polyamino-polycarboxylic acids and their derivatives.

The following are examples of possible complexing agents within the scope of the present invention:

Where n is 0, 1, or 2; R is —CF₂CO₂H; R₁ is —CF₂CONR₂R₃; and R₂ and R₃ are H, alkyl, mono or polyhydroxyalkyl, mono or polyalkoxyalkyl, or aryl groups. Specific examples of possible complexing agents within the scope of the present invention are:

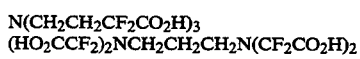

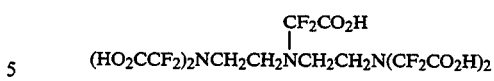

Other fluorinated complexing agents include the class of polyaminocarboxylic acid ligands in which free carboxylate groups are converted to fluorine-containing amides or esters. The following are examples of possible fluorinated amide and ester forms of polyaminocarboxylic acid ligands within the scope of the present invention:

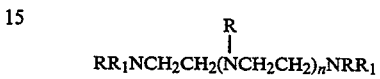

Where n is 0, 1, or 2; R is —CH₂CO₂H; R₁ is —CH₂CONR₂R₃; and R₂ and R₃ are fluorine substituted alkyl, mono or polyhydroxyalkyl, mono or polyalkoxyalkyl groups, or aryl groups. The aryl group may contain fluorine, hydroxy, mono or polyhydroxyalkyl, or mono or polyalkoxyalkyl substituents.

The following is an example of a possible cyclic fluorinated complexing agent within the scope of the present invention:

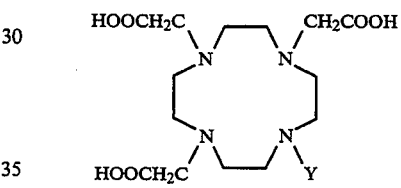

where Y may be —CH₂COOR₁ or —CH₂CONR₁R₂ and where R₁ and R₂ are CF₃, or fluorinated alkyl, mono or polyhydroxyalkyl, mono or polyalkoxyalkyl, or aryl having from 1 to 10 carbon atoms.

The following is an example of a fluorinated complexing agent designed for complexing manganese and iron ions:

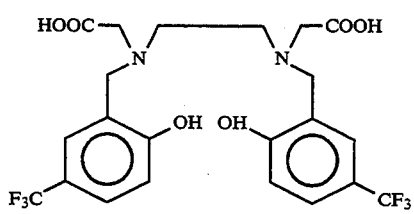

It will be appreciated by those skilled in the art that a large number of fluorinated complexing agents may be designed and prepared by fluorinating known complexing agents.

The fluorinated complexing agents within the scope of the present invention can be coupled as conjugates with biomolecules that are known to concentrate in the organ or tissues to be examined. These biomolecules include, for example, hormones such as insulin, prostaglandins, steroid hormones, amino sugars, peptides, proteins, lipids etc. Conjugates with albumins, such as human serum albumin, antibodies, monoclonal antibodies specific to tumor associated antigens, or antimyosin etc. The diagnostic media formed therefrom may be used in tumor and infarct diagnosis. Conjugates with liposomes are useful for liver imaging.

Although the foregoing discussion has focused on various fluorinated complexing agents for magnetic resonance imaging, it will be appreciated that the described magnetic resonance contrast media may be adapted for use in X-ray and ultrasound diagnosis. If the MRCM is intended for use in X-ray diagnosis, the central ion has to be derived from an element with a higher atomic number no achieve a sufficient absorption of X-rays. Elements with atomic numbers from 57 to 83 are suitable for this purpose.

Another class of fluorine-19 MRCM within the scope of the present invention are paramagnetic ion salts of fluorinated compounds. Either the anion or cation can be the fluorinated compound. The paramagnetic ion may include paramagnetic metal ions and paramagnetic free radical ions. The following are representative examples of possible paramagnetic ion salts of fluorinated compounds within the scope of the present invention:

(1) Paramagnetic ion is a free radical cation:

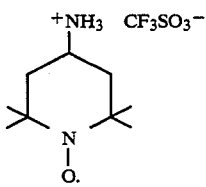

(2) Paramagnetic ion is a free radical anion:

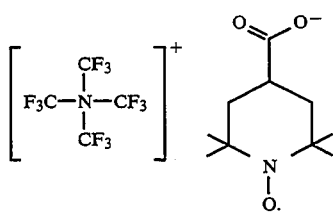

(3) Paramagnetic ion is a metal cation:

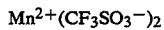

The $^{19}$F MRCM compounds of this invention are preferably formulated into diagnostic compositions for enteral or parenteral administration. The MRCM formulations may contain conventional pharmaceutical carriers and excipients appropriate for the type of administration contemplated.

For example, parenteral formulations for $^{19}$F imaging advantageously contain a sterile aqueous solution or suspension of a trifluoromethyl MRCM according to this invention. Various techniques for preparing suitable pharmaceutical solutions and suspensions are known in the art. Such solutions also may contain pharmaceutically acceptable buffers, stabilizers, antioxidants, and electrolytes, such as sodium chloride. Parenteral compositions may be injected directly or mixed with a large volume parenteral composition for systemic administration.

Formulations for enteral administration may vary widely, as is well-known in the art. In general, such formulations include a diagnostically effective amount of a $^{19}$F MRCM in an aqueous solution or suspension. Such enteral compositions may optionally include buffers, surfactants, adjuvants, thixotropic agents, and the like. Compositions for oral administration may also contain flavoring agents and other ingredients for enhancing their organoleptic qualities.

The diagnostic compositions within the scope of the present invention are administered in doses effective to achieve the desired enhancement of the NMR image. Such doses may vary widely, depending upon the degree fluorination, the organs or tissues which are the subject of the imaging procedure, the NMR imaging equipment being used, etc. Typical doses of the diagnostic compositions are in the range from about 0.005 to about 30 mmol/kg body weight, and preferably in the range from about 0.05 to about 5 mmol/kg body weight.

It has been found that the presence of paramagnetic species coupled to the fluorine-containing compound of the diagnostic compositions greatly improves the relaxation properties of $^{19}$F and the resulting $^{19}$F image. This lowers the doses required to obtain suitable diagnostic images and improves the safety of the diagnostic compositions.

The diagnostic compositions of this invention are used in a conventional manner in magnetic resonance procedures. Compositions may be administered in a sufficient amount to provide adequate visualization, to a warm-blooded animal either systemically or locally to an organ or tissues to be imaged, and the animal then subjected to the MRI procedure. The compositions enhance the magnetic resonance images obtained by these procedures.

The following examples are offered to further illustrate the present invention. These examples are intended to be purely exemplary and should not be viewed as a limitation on any claimed embodiment.

Example 1

Synthesis of spin labelled N-(2,3-dihydroxypropyl)-3,5-bis(trifluoromethyl)-benzenecarboxamide N-((2,2,5,5-Tetramethyl-1-pyrrolidinyloxy)methyl, free radical)-N-(2,3-dihydroxypropyl)-3,5-bis(trifluoromethyl)benzenecarboxamide, a spin labelled bis(-trifluoromethyl)-benzene derivative is prepared as follows: 3,5-bis(trifluoromethyl) benzoyl chloride (13.8 g, 50 mmol) in 50 mL of toluene is added to a solution of N-(2,3-dihydroxypropyl)-3 aminomethyl-2,2,5,5-tetramethyl-1-pyrrolidinyloxy, free radical (12.3 g, 50 mmol, prepared from 3-amino-1,2-propanediol and 3-bromomethyl-2,2,5,5-tetramethyl-1-pyrrolidinyloxy, free radical) and sodium bicarbonate (4.2 g, 50 mmol) in 50 mL of water. The heterogeneous mixture is stirred for 18 hours at room temperature. The mixture is poured into a separatory funnel. The aqueous layer is separated, washed with ether and evaporated. The residue purified by $C_{18}$ chromatography to give the spin labelled bis(trifluoromethyl)benzene derivative. The chemical reaction is shown below:

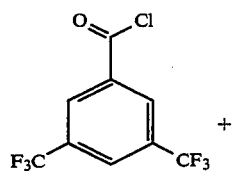

-continued

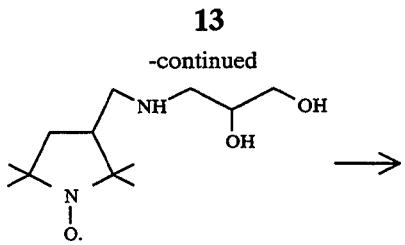

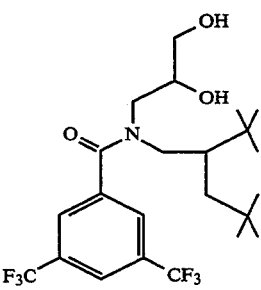

EXAMPLE 2

Synthesis of spin labelled N-(2,3-dihydroxypropyl)-3,5-bis(acetylamino)-2,4,6-tris(trifluoromethyl)benzenecarboxamide A mixture of 3,5-bis(acetylamino)-2,4,6-triiodobenzoyl chloride (32 g, 50 mmol), N-(2,3-dihydroxypropyl)-3-aminomethyl-2,2,5,5-tetramethyl-1-pyrrolidinyloxy, free radical (12.3 g, 50 mmol) and sodium bicarbonate (4.2 g, 50 mmol) in 100 mL of dimethyl formamide is stirred for 18 hours at room temperature. The solvent is evaporated under reduced pressure. The residue is purified by $C_{18}$ chromatography to give the spin labelled triiodobenzenecarboxamide. The chemical reaction is shown below:

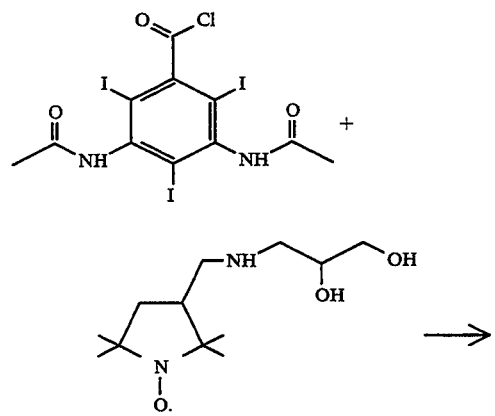

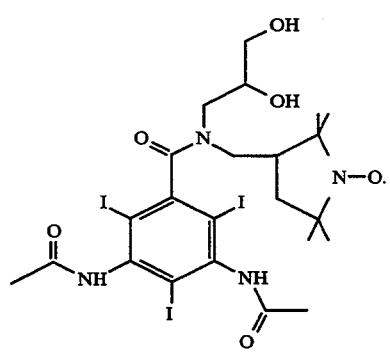

A mixture of N-((2,2,5,5-tetramethyl-1-pyrrolidinyloxy)methyl, free radical)-N-(2,3-dihydroxypropyl)-3,5-bis(acetylamino)-2,4,6-triiodobenzenecarboxamide (21 g, 25 mmol), sodium trifluoroacetate (61.2 g, 450 mmol) and copper(I) iodide (42.8 g, 225 mmol) in 500 mL of N,N dimethylacetamide is refluxed under argon for six hours. The solvent is evaporated under reduced pressure. The residue is purified by $C_{18}$ chromatography to give N-(( 2,2,5,5-tetramethyl-1-pyrrolidinyloxy)methyl, free radical)-N-(2,3-dihydroxypropyl)-3,5-bis-(acetylamino)-2,4,6-tris(trifluoromethyl)benzenecarboxamide. The chemical reaction is shown below:

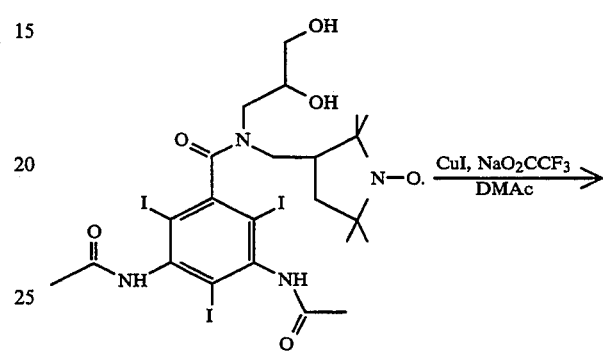

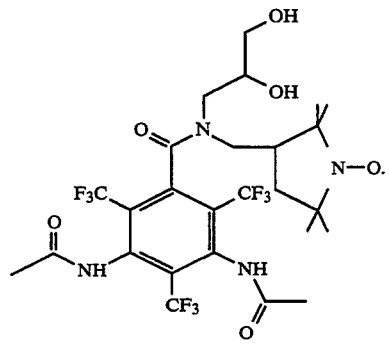

EXAMPLE 3

Synthesis of spin labelled N-(2,3-dihydroxypropyl)-2,3,5,6-tetrakis(trifluoromethyl)-1,4-benzenedicarboxamide 2,3,5,6-tetrakis(trifluoromethyl)-1,4-benzenedicarboxylic acid is prepared by charging a one liter stainless-steel autoclave with 1,2,4,5-benzenetetracarboxylic acid (51 g, 200 mmol) then cooled in liquid nitrogen. Hydrogen fluoride (100 g, 5.0 mol) and sulfur tetrafluoride (173 g, 1.6 mol) are added. The autoclave is sealed and heated at 150° C. for six hours. The gases are vented and the contents are poured onto ice. The mixture is transferred to a separatory funnel and extracted into ether. The ether layers are washed with dilute sodium hydroxide, dried over magnesium sulfate, filtered and evaporated to leave crude product. Recrystallization is used to give pure 1,2,4,5-tetrakis(trifluoromethyl)benzene. The chemical reaction is shown below:

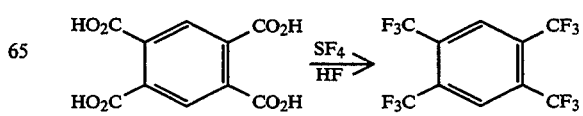

A solution of n-butyl lithium (6.4 g, 100 mmol) in hexanes is added at room temperature to a solution of 1,2,4,5-tetrakis(trifluoromethyl)benzene (16.9 g, 50 mmol) 200 mL of anhydrous ether under argon. After one hour the reaction mixture is poured onto dry ice. The mixture is taken up into water, washed with ether and acidified to pH 2. The product is extracted into ether, washed with water and brine, dried over magnesium sulfate, filtered and evaporated. The crude product is recrystallized to give 2,3,5,6-tetrakis(trifluoromethyl)-1,4-benzenedicarboxylic acid. The chemical reaction is shown below:

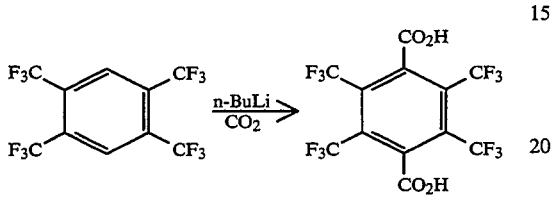

A mixture of thionyl chloride (11.9 g, 100 mmol) and 2,3,5,6-tetrakis(trifluoromethyl)-1,4-benzenedicarboxylic acid (22 g, 50 mmol) is refluxed in 100 mL of toluene for eight hours. The solvent is evaporated and the residue is distilled to give 2,3,5,6-tetrakis(trifluoromethyl)-1,4-benzenedicarboxylic acid chloride. The chemical reaction is shown below:

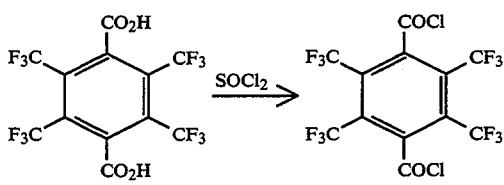

A mixture of 2,3,5,6-tetrakis(trifluoromethyl)-1,4-benzenedicarboxylic acid chloride (24 g, 50 mmol), N-(2,3-dihydroxypropyl)-3 aminomethyl-2,2,5,5-tetramethyl-1-pyrrolidinyloxy, free radical (25 g, 100 mmol) and sodium bicarbonate (8.4 g, 100 mmol) in 100 mL of dimethyl formamide is stirred for 18 hours at room temperature. The solvent is evaporated under reduced pressure. The residue is purified by $C_{18}$ chromatography to give the spin labelled tetrakis(trifluoromethyl)-benzene derivative. The chemical reaction is shown below:

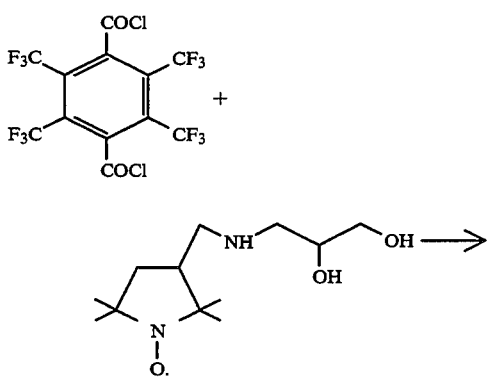

-continued

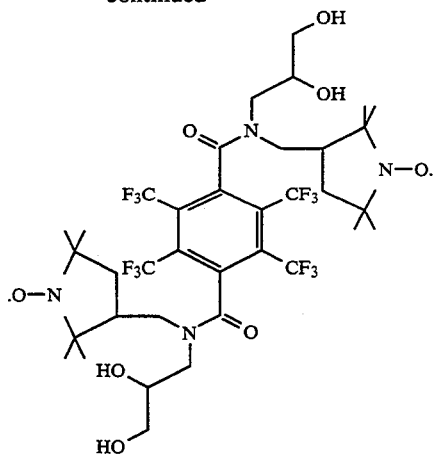

EXAMPLE 4

Synthesis of 2,5-dimethyl-2,5-ditrifluoromethyl-pyrrolidine-1-oxyl, free radical To a solution of trifluoromethylnitroethane (64.5 g, 0.50 mol) in 400 mL of methanol was added a solution of 25% sodium methoxide (21.6 g, 86.4 mL, 0.40 mol). To the resulting mixture was added dropwise trifluoromethyl methyl vinyl ketone (50 g, 0.40 mol). After stirring for 2 hours, glacial acetic acid (40.8 g, 39 mL, 0.68 mol) was added and the solvents were removed under reduced pressure. The residue was partitioned between ether and water (300 mL each) and the layers were separated. The ether layer was washed three times with 100 mL of 10% sodium carbonate solution followed by 100 mL of saturated sodium chloride solution. The solvent was evaporated and the residue was distilled to give the nitroketone (1), as shown in the following reaction:

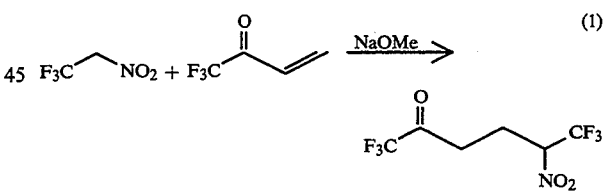

Portions of zinc dust (62.8 g, 0.96 mol) were added to a mechanically-stirred mixture of (1) (60 g, 0.24 mol) and ammonium chloride (12.8 g, 0.24 mol) in 350 mL of water cooled to 10° C. After the addition was complete, the mixture was stirred an additional 30 minutes and then filtered, washing the cake well with methanol. The filtrate was evaporated to 100 ML volume, saturated with borax and extracted several times with ether. The combined organic extracts were dried over anhydrous potassium carbonate and evaporated. The residue was distilled to give the nitrone (2), as shown in the following reaction:

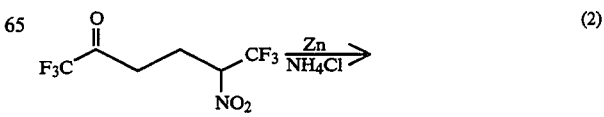

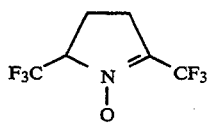

To nitrone (2) (20 g, 0.05 mol) in 50 mL anhydrous tetrahydrofuran at 0° C. under argon atmosphere was added dropwise a 1M solution of methyl magnesium chloride (55 mL, 0.055 mol). After the addition was complete, the reaction mixture was allowed to reach 25° C. and stirred to 20 hours. The reaction was cooled to 0° C. and sufficient saturated ammonium chloride solution was added to precipitate inorganic salts. The tetrahydrofuran solution was decanted, the residue was washed with additional tetrahydrofuran, and the combined extracts were evaporated to give an oil. The crude oil was dissolved in methanol (100 mL) and concentrated ammonium hydroxide (10 mL) and stirred with cupric acetate (0.90 g, 0.005 mol). Air was bubbled through the solution until a dark blue color persisted. The solution was washed successively with saturated sodium carbonate and saturated sodium chloride, dried over anhydrous potassium carbonate and evaporated to give (3), as shown in the following reaction:

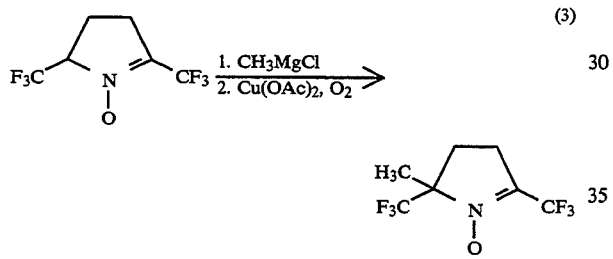

Crude (3) (5.0 g, 0.02 mol) was dissolved in 25 mL of anhydrous tetrahydrofuran and cooled to 0° C. under argon atmosphere. The a 1M solution of methyl magnesium chloride (22 mL, 0.022 mol) was added dropwise. The solution was allowed to slowly reach 25° C. and stirred for 20 hours. The same workup procedure outlined for (3) above was followed to give the desired nitroxide (4) as a crude gum, according to the reaction is shown below:

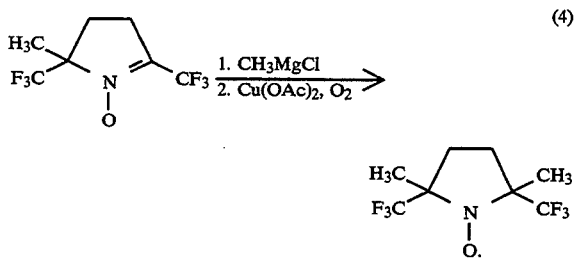

Further purification of (4) was achieved via chromatography over silica gel using an ether/hexane gradient as eluant.

EXAMPLE 5

Synthesis of meso-N,N'-Di-[bis(trifluoromethyl)-ethoxyacetyl]-2,3-diaminosuccinic acid Meso-2,3-diaminosuccinic acid (10.0 g, 67.6 mmol) was dissolved in 275 mL of 0.4913M sodium hydroxide solution (135) mmol) containing potassium carbonate (18.7 g, 135 mmol). A solution of 1,1-bis(trifluoromethyl) ethoxyacetic acid, N-hydroxysuccinimide active ester (45.5 g, 135 mmol) in 300 mL of ethyl acetate was added and the heterogeneous mixture was stirred overnight at room temperature. The layers were separated and the aqueous layer was acidified with 6N HCl and extracted with ethyl acetate. The combined organic layers were washed with water and brine, dried over magnesium sulfate, filtered and evaporated to leave a white solid. The solid was slurried in 150 mL of hot ethyl acetate, hexanes (150 mL) was added and the mixture cooled overnight. The solid was collected and recrystallized from methanol (150 mL)/water (300 mL) to afford 32.2 g (81%) of fine white powder after drying (100° C., 1.0 torr). $^1$H, $^{13}$C and $^{19}$F NMR spectra were consistent. Analysis calculated for $C_{16}H_{16}N_2O_8F_{12}$: C, 32.43; H, 2.7; N, 4.73; F, 38.51. Found: C, 32.31; H, 2.59; N, 4.54; F, 38.06. The chemical reaction is shown below:

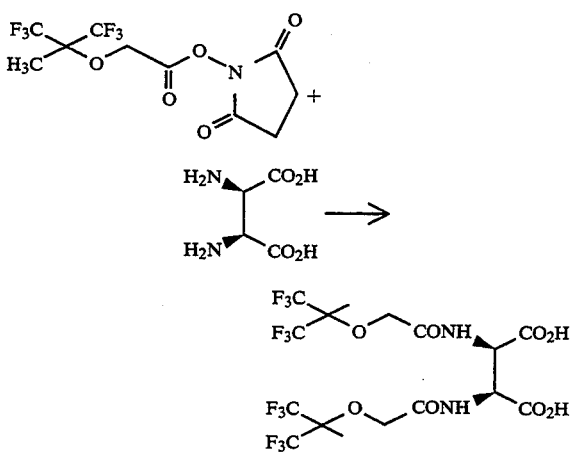

The meso-N,N'-di-[bis(trifluoromethyl)-ethoxyacetyl]-2,3-diaminosuccinic acid, in $^{19}$F relaxivity studies, had a $T_1$ of 1.08±0.006 seconds at a concentration of 30 mM. The long $T_1$ value results in a low $^{19}$F signal intensity.

EXAMPLE 6

Synthesis of meso-N,N'-Di-[1,1-bis(trifluoromethyl)-ethoxyacetyl]-2,3-diaminosuccinic acid, mono amide, N-2,2,6,6-tetramethylpiperidinyloxy, free radical Dicyclohexylcarbodiimide (6.95 g, 33.7 mmol) was added to a solution of meso-N,N'-di-[1,1-bis(trifluoromethyl)-ethoxyacetyl]-2,3-diaminosuccinic acid (20.0 g, 33.7 mmol) in 425 mL of dry tetrahydrofuran. After stirring for two hours at room temperature, the solution was cooled and the dicyclohexylurea was removed by filtration. The filtrate was evaporated. The residue was triturated with ether and isolated by filtration to afford 18.0 g (93%) of meso-N,N'-di-[1,1-bis(trifluoromethyl)ethoxyacetyl-]-2,3-diaminosuccinic anhydride. The anhydride (18.0 g, 31.4 mmol) and 4-amino-2,2,6,6-tetramethylpiperidinyloxy, free radical (4-amino-TEMPO, 5.36 g, 31.4 mmol) were refluxed together in 200 mL of acetonitrile for 5 minutes. The solvent was evaporated. The residue was dissolved in 0.5N sodium hydroxide and washed with ether. The aqueous layer was acidified with 6N HCl and extracted with ether. The combined ether layers were washed with water and brine, dried over magnesium sulfate, filtered and evaporated to leave an orange glass. This residue was chromatographed on a large plug of silica gel (methylene chloride followed by 5% methanol-/ethyl acetate). The clean fractions were combined and evaporated. The residue was triturated with hexanes to afford 17.5 g (75%) of fine orange powder after drying. $^1$H, $^{13}$C and $^{19}$F NMR spectra were consistent after reduction of the free radical with ascorbic acid. Analysis calculated for $C_{25}H_{33}N_4O_8F_{12}$: C, 40.27; H, 4.43, N, 7.52. Found: C, 39.82; H, 4.46; N, 7.33. The chemical reaction is shown below:

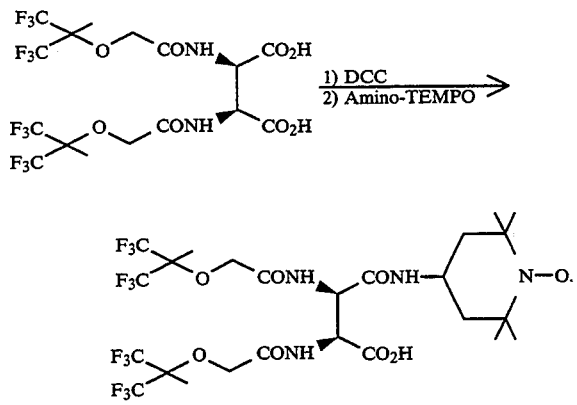

The meso-N,N'-di-[1,1-bis(trifluoromethyl)-ethoxyacetyl]-2,3-diaminosuccinic acid, mono amide, N-2,2,6,6-tetramethylpiperidinyloxy, free radical, in $^{19}$F relaxivity studies, had a $T_1$ of 0.0048 seconds at a concentration of 30 mM. The very short $T_1$ value results in a high $^{19}$F signal intensity.

From the foregoing, it will be appreciated that the present invention provides $^{19}$F magnetic resonance contrast media having enhanced $^{19}$F relaxivity. The fluorine-containing compounds have enhanced $^{19}$F relaxation properties resulting from direct association with an unpaired spin. The disclosed fluorine MRI agents enhance images of body organs and tissues and may be administered in relatively low concentrations, yet provide a clear, strong signal.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for obtaining fluorine-19 magnetic resonance images of body organs and tissues which comprises:
    (a) administering to a patient, a diagnostically effective amount of a fluorine-containing compound having enhanced relaxation properties resulting from direct association with a nitroxide; and
    (b) imaging the patient's organs and tissues.

2. A method for obtaining fluorine-19 magnetic resonance images as defined in claim 1, wherein the fluorine-containing compound administered to the patient has a stable nitroxide covalently attached to the fluorine-containing compound.

3. A method for obtaining fluorine-19 magnetic resonance images of body organs and tissues which comprises:
    (a) administering to a patient, a diagnostically effective amount of a spin labelled tris(trifluoromethyl)-benzene derivative in a pharmaceutically acceptable carrier, said spin labelled tris(trifluoromethyl)-benzene derivative having a general formula:

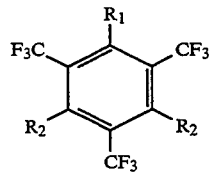

where $R_1$ is $CONR_3R_4$, $NR_3R_4$, or $NHCOCH_2NR_3R_4$; $R_2$ is $CONHR_3$, $NHCOCH_2NHR_3$, $NHR_3$, $CO_2^-$, or $CO_2H$; $R_3$ is H or a hydroxyalkyl group; and $R_4$ is a nitroxide; and
    (b) imaging the patient's organs and tissues.

4. A method for obtaining fluorine-19 magnetic resonance images of body organs and tissues which comprises:
    (a) administering to a patient, a diagnostically effective amount of a spin labelled bis(trifluoromethyl)-benzene derivative in a pharmaceutically acceptable carrier, said spin labelled bis(trifluoromethyl)-benzene derivative having a general formula:

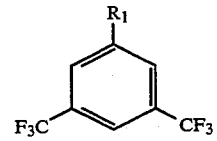

where $R_1$ may be $-CONR_3R_4$, $-NR_3R_4$, $-NHCOCH_2NR_3R_4$, and pharmaceutically acceptable salts thereof; $R_3$ may be H or hydroxyalkyl; and $R_4$ is a nitroxide; and
    (b) imaging the patient's organs and tissues.

5. A method for obtaining fluorine-19 magnetic resonance images of body organs and tissues which comprises:
    (a) administering to a patient, a diagnostically effective amount of a spin labelled tetrakis(trifluoromethyl)benzene derivative in a pharmaceutically acceptable carrier, said spin labelled tetrakis(trifluoromethyl)benzene derivative having a general formula:

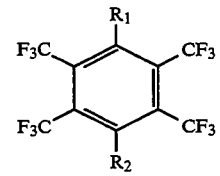

where $R_1$ is $CONR_3R_4$, $NR_3R_4$, or $NHCOCH_2NR_3R_4$; $R_2$ is $CONHR_3$, $NHCOCH_2NHR_3$, $NHR_3$, $CO_2^-$, or $CO_2H$; $R_3$ is H or a hydroxyalkyl group; and $R_4$ is a nitroxide; and
    (b) imaging the patient's organs and tissues.

6. A diagnostic composition suitable for enteral or parenteral administration to a patient comprising:

a diagnostically effective amount of a spin labelled tris(trifluoromethyl)benzene derivative having a general formula:

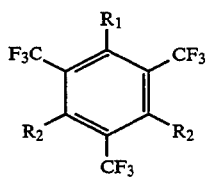

where $R_1$ is $CONR_3R_4$, $NR_3R_4$, or $NHCOCH_2NR_3R_4$; $R_2$ is $CONHR_3$, $NHCOCH_2NHR_3$, $NHR_3$, $CO_2^-$, or $CO_2H$; $R_3$ is H or a hydroxyalkyl group; and $R_4$ is a nitroxide; and a pharmaceutically acceptable carrier.

7. A diagnostic composition suitable for enteral or parenteral administration to a patient comprising:

a diagnostically effective amount of a spin labelled bis(trifluoromethyl)benzene derivative having a general formula:

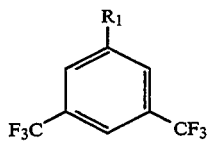

where $R_1$ may be $-CONR_3R_4$, $-NR_3R_4$, $-NHCOCH_2NR_3R_4$, and pharmaceutically acceptable salts thereof; $R_3$ may be H or hydroxyalkyl; and $R_4$ is a nitroxide; and a pharmaceutically acceptable carrier.

8. A diagnostic composition suitable for enteral or parenteral administration to a patient comprising:

a diagnostically effective amount of a spin labelled tetrakis(trifluoromethyl)benzene derivative having a general formula:

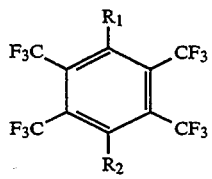

where $R_1$ is $CONR_3R_4$, $NR_3R_4$, or $NHCOCH_2NR_3R_4$; $R_2$ is $CONHR_3$, $NHCOCH_2NHR_3$, $NHR_3$, $CO_2^-$, or $CO_2H$; $R_3$ is H or a hydroxyalkyl group; and $R_4$ is a nitroxide; and a pharmaceutically acceptable carrier.

* * * * *